| United States Patent [19] | [11] Patent Number: 4,505,901 |
| El-On et al. | [45] Date of Patent: Mar. 19, 1985 |

[54] COMPOSITIONS AND METHODS FOR TOPICAL TREATMENT OF CUTANEOUS LEISHMANIASIS WITH PAROMOMYCIN

[75] Inventors: Joseph El-On; Geoffrey P. Jacobs, both of Jerusalem, Israel

[73] Assignee: Orvet B.V., Holland, N.Y.

[21] Appl. No.: 477,741

[22] Filed: Mar. 22, 1983

[30] Foreign Application Priority Data

Mar. 29, 1982 [GB] United Kingdom ................. 8209231

[51] Int. Cl.$^3$ ...................... A61K 31/71; C07H 15/22
[52] U.S. Cl. ...................................... 514/38; 424/45; 536/13.3
[58] Field of Search ......................... 424/180, 181, 45; 536/13.3

[56] References Cited

U.S. PATENT DOCUMENTS

| 2,916,485 | 12/1959 | Frohardt et al. | 536/13.3 |
| 3,711,602 | 1/1973 | Herschler | 424/45 |
| 3,743,727 | 7/1973 | Herschler | 424/181 |
| 3,897,412 | 7/1975 | Naito et al. | 536/13.3 |

*Primary Examiner*—Johnnie R. Brown
*Attorney, Agent, or Firm*—Steinberg & Raskin

[57] ABSTRACT

The compositions contain a mixture of paromomycin or a non-toxic acid addition salt thereof and dimethylsulfoxide or a quaternary ammonium salt having topical anti-infective activity, together with an inert carrier. There is also provided a method for the topical treatment of a patient against cutaneous leishmaniasis comprising applying to lesions of such disease a composition as specified.

18 Claims, No Drawings

COMPOSITIONS AND METHODS FOR TOPICAL TREATMENT OF CUTANEOUS LEISHMANIASIS WITH PAROMOMYCIN

The present invention concerns compositions for the topical treatment of cutaneous leishmaniasis.

Leishmaniasis includes a variety of disease syndromes caused by Leishmania species and poses an important public health problem. It is still the cause of considerable mortality and morbidity and results in variable disfigurement of the affected individuals. The disease has recently been recognized by the WHO as one of the six major tropical diseases. Three general forms of the disease exist: visceral (kala-azar), cutaneous and muco-cutaneous. In kala-azar, or in certain cases of cutaneous and mucocutaneous leishmaniasis, the disease can progress to death. The leishmaniases occur over a relatively large part of the world from China across Asia, India, Persia and Afghanistan, the Caucasus, the Middle and Near East, the Mediterranean basin, East and West Africa, the Sudan and Latin America.

The Jordan Valley, the eastern shore of the Dead Sea, Aravah and the Israeli Negev are hyperendemic areas of Israel for cutaneous leishmaniasis (Gunders et al. Trans.R. Soc. Trop. Med. Hyg. 1972, 66, 235–238; Nagan et al. Trans. R. Soc. Trop. Med. Hyg. 1972, 66, 239–243). Locally, the disease is commonly called "Rose of Jericho". Although vaccination with fully pathogenic organisms is practised (Handman et al. J. Biol. Stand. 1974, 2, 223–229; (Koufman et al. Israel J. Med. Sci. 1978, 14, 218–222), there is no full agreement as to its efficacy. Therapeutic methods are even more disputed and there is no general consensus on available medications.

The number of effective drugs against the disease is extremely small (Newton, in Trypanosomiasis and Leishmaniasis, Elliot et al. eds. 1974, p. 285; Peters, in Trypanosomiasis and Leishmaniasis, Elliot et al. eds. 1974, p. 236; Williamson, Trans. R. Soc. Trop. Med. Hyg., 1974, 70, 117–119). Treatment with one of the few leishmanicidal agents may produce apparent or genuine cure in most patients but a significant porportion does not readily respond. Chemotherapy is dependent for the most part upon two groups of compounds, the pentavalent antimonials and the diamidines. The effectiveness of the drugs is variable. All the antileishmanial drugs available are given systematically by either I.M. or I.V. administration.

Moskalenko and Pershin, Pharmakol. I. Toxikol. 1966, 29(1), 90–94 have reported a high chemotherapeutic effect of paromomycin and monomycin, at that time believed to be two different antibiotics of the neomycin group of antibiotics, but subsequently shown to be identical, in experimental cutaneous leishmaniasis of albino mice. Similar experiments were reported by Neal, Ann. Trop. Med. Parasitol. 1968, 62(1), 54–62. In both cases the drugs were injected subcutaneously and in summing up his results Neal states that while monomycin and paromomycin were about 100 times more active than sodium stibogluconate, this high activity was offset by the toxicity after parenteral administration.

It is also noteworthy that in a recent survey on aminoglycosides (Bailey, Drugs 22, 321–327 (1981)), paromomycin is stated to have no clinical place.

Thus, the conventional treatment of cutaneous leishmaniasis remains to date injection of organic antimony compounds such as sodium stibogluconate, which however is painful and can provide serious side effects. Moreover, quite generally, administration of a drug by injection is never very convenient. Consequently, investigators in the field have for long been looking for a pharmaceutical composition that can be applied topically.

One such composition is described in U.K. Patent Application No. 2,038,626 of Jan. 4, 1979, published on July 30, 1980. This composition comprises γ-benzenehexachloride, tetraethylthiuram monosulfide and a keratoplastic agent, such as salicylic acid, in an ointment or cream base. However, no evidence was presented that this composition is effective. Moreover, it is well known that γ-benzenehexachloride is a highly toxic compound which is used as insecticide.

It is the object of the present invention to provide an effective composition for the topical treatment of cutaneous leishmaniasis.

In accordance with the present invention it has now surprisingly been found that while paromomycin on the one hand is only very slightly active topically and various quaternary ammonium salts with topical anti-infective activity as well as dimethylsufloxide (DMSO) on the other hand are all topically ineffective against cutaneous leishmaniasis, a mixture of paromomycin or a non-toxic acid addition salt thereof with any of these quaternary ammonium salts or DMSO is highly effective both symptomatically and therapeutically. It is thus evident that the above quaternary ammonium salts and DMSO increase considerably the cutaneous therapeutic effect of paromomycin which was completely surprising and unexpected.

Based on these surprising observations the invention provides a composition for the topical treatment of cutaneous leishmaniasis comprising paromyomycin or a non-toxic acid addition salt thereof, at least one member selected from the group consisting of dimethylsufoxide and quaternary ammonium salts having topical anti-infective activity, and an inert carrier.

In the following a member of the group of compounds consisting of dimethylsulfoxide and quaternary ammonium salts having topical anti-infective activity will be referred to, for short, as "second component".

A practical range for the contents of paromomycin or its non-toxic addition salt in a composition according to the invention is from 5 to 40% by weight, a preferred range being from 10 to 20% by weight. A content of about 15% by weight has been found in particular suitable.

There are no critical limitations on the relative proportions between paromomycin or its nontoxic salt on the one hand and the second component on the other hand. By way of example, a 1:1 w/w ratio has been found suitable.

The compositions according to the invention can be in form of ointments and creams. In case of an ointment or cream, any conventional carrier can be used such as, for example, white soft paraffin (WSP), hard paraffin, white vaseline and the like. Lotions can, for example be aqueous and in this case the carrier is water.

Examples of quaternary ammonium salts that serve as second components are methylbenzethonium chloride, benzethonium chloride, benzalkonium chloride, cetalkonium chloride and cetrimonium bromide (Cetrimide B.P.). All these are known compounds as is dimethylsulfoxide.

The following are a few examples of ointments according to the invention, all percentages being by weight:

| | | |
|---|---|---|
| 1. | Paromomycin | 15% |
| | Methylbenzethonium chloride | 12-15% |
| | WSP | balance |
| 2. | Paromomycin | 15% |
| | Benzalkonium chloride | 12% |
| | WSP | balance |
| 3. | Paromomycin | 15% |
| | DMSO | 12% |
| | WSP | balance |
| 4. | Paromomycin | 15% |
| | Cetalkonium chloride | 15% |
| | WSP | balance |
| | Paromomycin | 15% |
| | Cetrimonium bromide | 15% |
| | WSP | balance |

In all these compositions the relative amount of paromomycin is calculated as free base but the substance was introduced in form of the sulfat.

If desired, the compositions may also contain water.

These and similar ointments are prepared by simply mixing the constituents in the desired proportions.

The following is an example of a cream according to the invention:

| | |
|---|---|
| Paromomycin (as sulfate) | 15% |
| Methylbenzethonium chloride | 12% |
| Base | 50% |
| Preservatives | 0.15% |
| EDTA | 0.07% |
| Sodium metabisulfite | 0.01% |
| Water | q.s |
| Composition of base | |
| Cetyl alcohol | 13% |
| Stearic acid | 20% |
| Hard paraffin | 5% |
| Paraffin liquid (heavy) | 25% |
| Glyceryl monostearate | 22% |
| White vaseline | 15% |

The cream base is prepared by heating the components to 70° C., mixing and cooling.

For preparation of the cream, the base is heated to 70° C. The active ingredients and the preservatives are dissolved in purified water at 70° C. The water phase is added slowly to the oily phase while mixing.

The effects of compositions according to the invention were demonstrated by a series of tests reported below:

TEST REPORT NO. 1

Animals

Balb/c and C$_3$H/He mice, 8-12 weeks old were mainly used for in vivo studies of *L. tropica*. Guinea pigs were used for in vivo studies of *L. enriettii*.

Strains of Leishmania and their maintenance

A high virulent strain of *L. tropica*, LRC-L137, isolated from an Israeli case of simple cutaneous leishmaniasis in 1967 was used. This strain and the *L. enriettii* strain were obtained from the strain collection of the WHO International Reference Centre for Leishmaniasis (LRC), maintained at the Department of Medical Parasitology, The Hebrew University-Hadassah Medical School, Jerusalem. The parasites were kept as stabilates in liquid nitrogen, and were used for each experiment after their cultivation on blood agar at 27° C. *L. tropica* LRC L-137 was also maintained in vivo in male hamster.

The effect of drugs on *L. tropica* development

The effect of the drug on in vivo development on *L. tropica* was monitored in inbred mice by following the development of local dermal lesions caused by the parasites. Balb/c mice were inoculated in the base of the tail with $1-5 \times 10^6$ infective promastigotes. The development of the lesions was followed weekly. The presence and absence of amastigotes in the lesions was shown by preparing an air-dried film of material from the lesion after straining with Giemsa stain.

The ointment was administered topically to the lesion, twice daily for 10 days or more, starting at least 20 days post infection.

The development of the lesion was followed macroscopically and the presence of parasites in biopsy material was monitored microscopically in both smear and cultures.

In one series of tests the combined ointment compositions according to the invention comprising paromomycin and methylbenzethonium chloride were compared with similar methylbenzethonium chloride ointment compositions comprising other antibiotics. In a second series of tests paromomycin was compounded with various second components.

The results obtained in these tests are tabulated in the following Table 1.

The first part of Table 1 shows results of tests with six compositions each containing an antibiotic and 11-13% by weight of methylbenzethonium chloride, and of one blank test with a composition without an antibiotic.

The second part of the Table shows results of tests with four compositions according to the invention containing each 15% by weight of paromomycin and 12% by weight of different second components, and of one blank test of a paromomycin composition without any second component.

TABLE 1

The effect of topical treatment with different ointments on *L. tropica* and *L. enriettii* development in mice and guinea pigs

| Ointment Formulation | Number of mice | Duration of Treatment (days) | Drug efficacy (smears and/or cultures) - Days after treatment termination | | | | | | | | |
|---|---|---|---|---|---|---|---|---|---|---|---|
| | | | 5 | 10 | 15 | 20 | 30 | 40 | 50 | 60 | 70 | 80 |
| 11-13% methylbenzethonium chloride | | | | | | | | | | | | |
| 15% neomycin[a] | 5 | 11 | 0/5[b] | | | | | 0/5 | | 0/5 | | 0/3 |
| 15% kanamycin[a] | 5 | 11 | 5/5 | | | 1/5 | | | | 0/4 | | 0/1 |

TABLE 1-continued

The effect of topical treatment with different ointments on L. tropica and
L. enriettii development in mice and guinea pigs

| Ointment Formulation | Number of mice | Duration of Treatment (days) | Drug efficacy (smears and/or cultures) - Days after treatment termination | | | | | | | | | |
|---|---|---|---|---|---|---|---|---|---|---|---|---|
| | | | 5 | 10 | 15 | 20 | 30 | 40 | 50 | 60 | 70 | 80 |
| 15% gentamicin[a] | 5 | 11 | 5/5 | 2/4 | 1/4 | | 1/4 | 1/3 | 1/3 | | 1/2 | 1/1 |
| 15% paromomycin[a] | 8 | 10 | 8/8 | | | | | 8/8 | 8/8 | 8/8 | | 8/8 |
| 15% paromomycin[a] | 3* | 10 | 3/3 | | | | | | | | | 3/3 |
| 15% rifampicin | 8 | 10 | 5/8 | | 3/8 | | 3/8 | 2/8 | 0/8 | 0/8 | | 0/8 |
| none | 8 | 10 | 3/8 | 1/8 | | | 0/8 | | | | | |
| 15% paromomycin | | | | | | | | | | | | |
| 12% benzethonium chloride | 5 | 10 | 5/5 | | 5/5 | | 5/5 | | | 5/5 | 5/5 | 5/5 |
| 12% cetalkonium chloride | 5 | 10 | 5/5 | | 5/5 | | 5/5 | | 5/5 | | 4/5 | 4/5 |
| 12% DMSO | 10 | 10 | 10/10 | 10/10 | | | | | | 10/10 | | 9/10 |
| 12% benzalkonium chloride | 10 | 10 | 2/7 | | | | | 2/2 | | 2/2 | | 2/2 |
| none | 7 | 12 | 2/7 | 1/7 | | | | | 0/7 | | | |

*Guinea pig
[a] as sulfates

[b] results are expressed as: $\frac{\text{number of mice cleared}}{\text{number of living mice}}$ From the first part of the Table which sums up the first series of tests, it is seen clearly that only the paromomycin compositions show a therapeutic effect after 80 days from the termination of the treatment. Some results were also produced by getamicin, but these were not lasting.

The second part of the Table shows that all the various paromomycin composition with second components according to the invention produce excellent therapeutic results 80 days after the termination of the treatment with the one exception of paromomycin+benzalkonium chloride. Also in that case the surviving animals were cured but some animals died beforehand, possibly because the benzalkonium content was too high.

TEST REPORT NO. 3

The effect of anti-leishmanial ointments containing 15% paromomycin and different concentrations of methyl benzethonium chloride on L tropica in BALB/c mice Test animals: BALB/c mice
Infective agent: L tropica, 7 × 10⁶ promastigotes in base of tail.
Start of treatment: 71 days after infection
Treatment with:

| Lab code | J-16042 | J-16044/4 | /1 | /7 |
|---|---|---|---|---|
| Paromomycin (%) | 15 | 15 | 15 | 15 |
| Methyl benzethonium-chloride (%) | 2 | 1 | 0.1 | 0 |
| Duration of treatment (days) | 6 | 6 | 6 | 6 |

TABLE 2

| Ointment | | No. of mice | Before treatm | Results — Days after termination of treatment | | | | | |
|---|---|---|---|---|---|---|---|---|---|
| | | | | 2 | | 18 | | 41 | |
| P* | M* | | S | S | C | S | C | S | C |
| 15 | 2 | 5 | 0/5 | 5/5 | 3/5 | 5/5 | 4/5 | 5/5 | 4/5 |
| 15 | 1 | 5 | 0/5 | 3/5 | 2/5 | 4/5 | 4/5 | 3/5 | 3/5 |
| 15 | 0.1 | 5 | 0/5 | 0/5 | 0/5 | 4/5 | 3/5 | 3/5 | 3/5 |
| 15 | 0 | 5 | 0/5 | 3/5 | 1/5 | 2/5 | 1/5 | 1/5 | 0/5 |

Remarks
P: paromomycin
S: smears
M: methyl benzethonium chloride
C: cultures

Results are expressed as: $\frac{\text{number of mice cleared}}{\text{number of living mice}}$

Conclusion

The results obtained with the ointment containing 15% paromomycin and 2% methylbenzethonium chloride are comparable to those obtained with the ointment containing 15% paromomycin and 12% methylbenzethonium chloride.

Test Report No. 3

The effect of anti-leishmanial ointment containing 15% paromomycin and 2% methylbenzethonium chloride on L tropica from Saudi Arabia Test animals: BALB/c mice
Infective agent: L tropica (Saudi Arabia) 5 × 10⁶ promastigotes in base of tail
Start of treatment: 44 days after infection
Treatment with: Lab code: J-16042
Duration of treatment: 10 days

TABLE 3

| No. of mice | Before treatm | Results | | Days after termination of treatment | | | |
|---|---|---|---|---|---|---|---|
| | | 6th day of treatment | | 7 | | 30 | |
| | S | S | C | S | C | S | C |
| 4 | 0/4 | 4/4 | 3/4 | 4/4 | 4/4 | 4/4 | 4/4 |

Remarks
S: smears
C: cultures

Results are expressed as: $\frac{\text{number of mice cleared}}{\text{number of living mice}}$

Conclusion 10 days of treatment with the ointment cleared all mice of parasites.

TEST REPORT NO. 4

The effect of different concentrations of paromomycin sulfate in 12% methylbenzethonium chloride on the development of L. tropica was demonstrated in Balb/c mice.

Materials and Methods

Balb/c mice were used. Treatment was started about 60 days after infection with 5×10⁶ L. tropica promastigotes, when lesions were well developed. The mice were treated twice daily for 10 days.

Results

The effect of treatment is shown in the following Table 4. Day 0 is the last day of treatment.

TABLE 4

| percentage paromomycin (as sulfate) | No. of mice | days after termination of treatment | | | | | 47[x] |
|---|---|---|---|---|---|---|---|
| | | 2 | | 14 | | 26 | |
| | | s | c | s | c | s | c | |
| 1% | 5 | 5/5 | 5/5 | 5/5 | 5/5 | 1/5 | all mice with scabs |
| 5% | 5 | 5/5 | 5/5 | 5/5 | 5/5 | 5/5 | cured |
| 10% | 5 | 5/5 | 5/5 | 5/5 | 5/5 | 5/5 | cured |
| 15% | 5 | 5/5 | 5/5 | 5/5 | 5/5 | 5/5 | cured |

[x]macroscopic examination
s smear
c culture

Results are expressed as $\frac{\text{number of mice cleared}}{\text{number of living mice}}$

TEST REPORT NO. 5

The effectiveness of the synergistic compositions according to the invention was also demonstrated clearly on human patients. In a first series of tests 8 patients suffering from multiple lesions of cutaneous leishmaniasis, 7 (87%) recovered 7-12 days after treatment with 15% paromomycin (as sulfate) and 12% methylbenzethonium chloride in soft paraffin. The parasites were eliminated only from the treated lesions, while the untreated lesions of the same patients were found to contain living parasites. Total recovery from the disease occurred only after all the lesions had been treated. The eighth patient who was highly susceptible to infection and had well-developed granulomata at all the sites of infection, responded poorly to treatment. In this case only partial improvement was observed and the parasites were detectable even after 28 days of treatment.

These results are summed up in the following Table 5:

TABLE 5

The effect of 15% paromomycin (as sulfate) with 12% methylbenzethonium chloride in white soft paraffin on cutaneous leishmaniasis in patients

| Patient Number | Sex | Age (years) | Number of lesions | Distribution of lesions | Duration of treatment (days) | Recovery from infection |
|---|---|---|---|---|---|---|
| 1 | female | 18 | 4 | face - 2 hand - 2 | 10 | complete |
| 2 | female | 18* | 2 | face - 2 | 7 | complete |
| 3 | female | 22 | 4 | face - 2 hand - 2 | 10 | complete |
| 4 | male | 20 | 3 | neck - 2 leg - 1 | 12 | complete |
| 5 | male | 20 | 2 | hand - 1 chin - 1 | 14 | complete |
| 6 | male | 20 | 2 | chin - 1 elbow - 1 | 10 | complete |
| 7 | male | — | 5 | face - 1 nose - 1 hand - 3 | 10 | complete |
| 8 | male | 35** | 4 | face - 1 hands - 3 | 28 | partial |

*Previously treated with rifampicin for 30 days without any improvement
**Large lesions with granulomata.

Further examination of another 30 patients suffering from multiple lesions of cutaneous leishmaniasis indicated again the effectiveness of the synergistic compositions according to the invention. Of the 30 patients treated with the composition, 24 (80%) recovered from the infection.

TEST REPORT NO. 6

Three patients with cutaneous leishmaniasis were treated for 10 days with antileishmanial ointment containing 15% paromomycin and 1% methylbenzethonium chloride. Smears and cultures of treated lesions were negative after 10 days of treatment.

We claim:

1. Composition for the topical treatment of cutaneous leishmaniasis, said composition comprising a carrier for topical administration having distributed therethrough a quaternary ammonium salt selected from the group consisting of methylbenzethonium chloride, benzethonium chloride, benzalkonium chloride, cetalkonium chloride and centrimonium bromide, and paromomycin or a non-toxic acid addition salt thereof in an amount which with said quaternary ammonium salt constitutes a cutaneous leishmaniasis treatment effective amount.

2. Composition according to claim 1 wherein said paromomycin or non-toxic acid addition salt thereof is present in an amount of about 5-40% by weight.

3. Composition according to claim 1 wherein said paromomycin or non-toxic acid addition salt thereof is present in an amount of about 10-20% by weight.

4. Composition according to claim 1 wherein said paromomycin or non-toxic acid addition salt thereof is present in an amount of about 15% by weight.

5. Composition according to claim 1 wherein the amount of said quaternary ammonium salt is about 2-15% by weight.

6. Composition according to claim 2 wherein the amount of said quaternary ammonium salt is about 2-15% by weight.

7. Composition according to claim 3 wherein the amount of said quaternary ammonium salt is about 2-15% by weight.

8. Composition according to claim 4 wherein the amount of said quaternary ammonium salt is about 2-15% by weight.

9. Method for the topical treatment of cutaneous leishmaniasis, which comprises applying to lesions of a patient suffering from the same a composition comprising a quaternary ammonium salt selected from the group consisting of methylbenzethonium chloride, benzethonium chloride, benzalkonium chloride, cetalkonium chloride and cetrimonium bromide and paromomycin or a non-toxic acid addition salt, thereof in an amount which with said quaternary ammonium salt constitutes a cutaneous leishmaniasis treatment effective amount.

10. Method according to claim 9 wherein said composition is distributed in a carrier for topical administration.

11. Method according to claim 10 wherein the amount of said paromomycin or non-toxic acid addition salt is about 5-40% by weight.

12. Method according to claim 10 wherein the amount of said paromomycin or non-toxic acid addition salt is about 10-20% by weight.

13. Method according to claim 10 wherein the amount of said paromomycin or non-toxic acid addition salt is about 15% by weight.

14. Method according to claim 11 wherein the amount of said quaternary ammonium salt is about 2–15% by weight.

15. Method according to claim 12 wherein the amount of said quaternary ammonium salt is about 2–15% by weight.

16. Method according to claim 13 wherein the amount of said quaternary ammonium salt is about 2–15% by weight.

17. Method according to claim 11 wherein said quaternary ammonium salt is in approximately 1:1 weight proportion with said paromomycin or non-toxic acid addition salt thereof.

18. Composition according to claim 2 wherein said quaternary ammonium salt is present in an approximately 1:1 weight proportion with said paromomycin or non-toxic acid addition salt thereof.

* * * * *